US00PP11530P

United States Patent [19]

Tiemann

[11] Patent Number: Plant 11,530

[45] Date of Patent: Sep. 26, 2000

[54] SWEET CHERRY TREE NAMED 'JORK 57/201'

[75] Inventor: Karl-Heinz Tiemann, Hamburg, Germany

[73] Assignee: Jork Fruit Research Station, Jork, Germany

[21] Appl. No.: 09/018,696

[22] Filed: Feb. 4, 1998

[51] Int. Cl.[7] ..... A01H 5/00

[52] U.S. Cl. ..... Plt./181

[58] Field of Search ..... Plt./181

[56] References Cited

U.S. PATENT DOCUMENTS

P.P. 8,721 5/1994 Calder ..... Plt./181

*Primary Examiner*—Howard J. Locker

*Assistant Examiner*—Wendy A Baker

*Attorney, Agent, or Firm*—Klarquist Sparkman Campbell Leigh & Whinston LLP

[57] ABSTRACT

A new and distinct variety of sweet cherry tree named 'Jork 57/201' characterized by: excellent tolerance to rain-induced fruit splitting; blooms 3–4 days later than 'Bing' (one of the latest blooming among late-blooming varieties); one of the best of late-blooming varieties in terms of fruit size and quality; the color of the stem and of the unfolded and partially unfolded leaves are different than 'Bing'; flowers open later than most other cultivars; and pedicels are shorter and a darker shade of yellow-green than 'Bing'.

2 Drawing Sheets

The present invention relates to a new and distinct variety of sweet cherry tree, referred to by the varietal name 'Jork 57/201'.

The parent tree(s) of the new variety was discovered in a cultivated area in Jork, Hannover, Germany. 'Jork 57/201' was selected from among seedlings resulting from the cross 'Schneiders Spate Knorpelkirsche'×'Rube' (both believed to be unpatented). My new variety has been asexually reproduced by grafting on 'F12/1' rootstock (believed to be unpatented) at the Fruit Experiment Station, Jork, Germany.

This invention has not been observed under all possible environmental conditions. However, the following combination of traits have been repeatedly observed in asexually propagated progeny and are determined to be the basic characteristics of this invention, which in combination distinguish this variety of sweet cherry as a new and distinct variety: excellent tolerance to rain-induced fruit splitting; blooms 3–4 days later than 'Bing' (believed to be unpatented, one of the latest blooming among late-blooming varieties); one of the best of late-blooming varieties in terms of fruit size and quality; the color of the stem and of the unfolded and partially unfolded leaves are different than 'Bing'; flowers open later than most other cultivars; and pedicels are shorter and a darker shade of yellow-green than 'Bing'.

Asexual reproduction by grafting on 'F12/1' rootstock in Jork, Germany shows that these characteristics are established and transmitted through succeeding asexual propagations.

BRIEF DESCRIPTION OF THE PHOTOGRAPHS

The accompanying photographs depict the color of the fruit and other parts of my new cherry variety as nearly true as is reasonably possible to make the same in color illustrations of this character.

DETAILED DESCRIPTION

Figure 1:
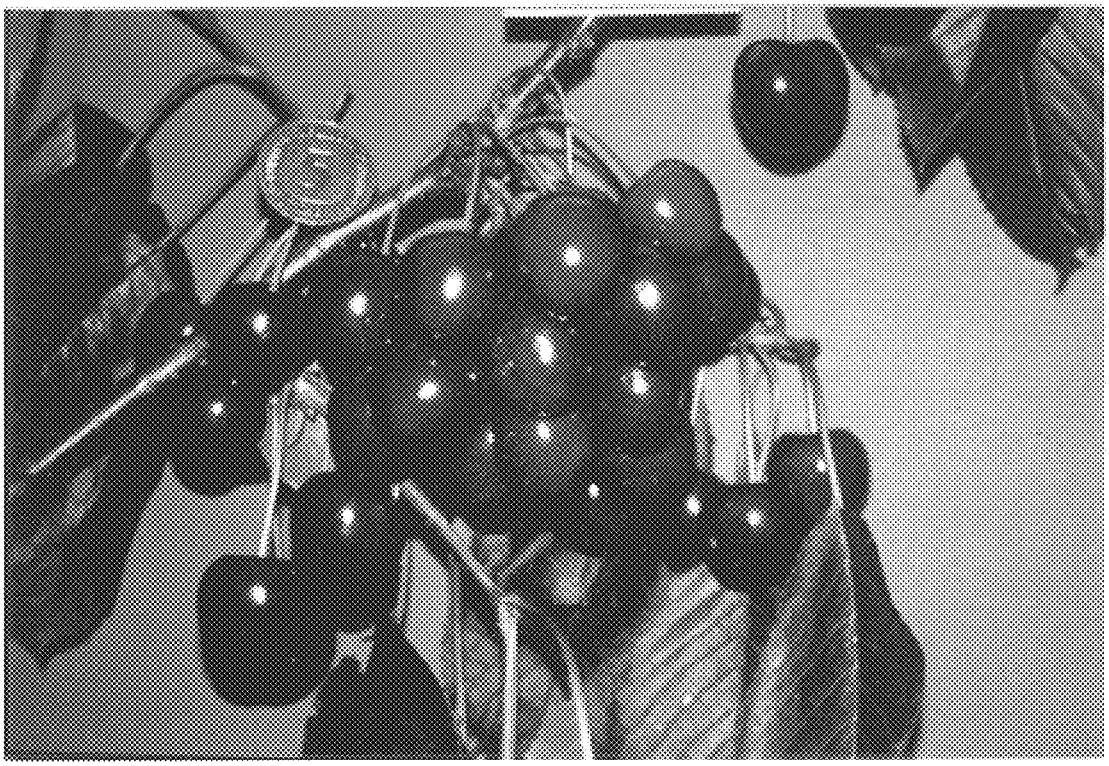
FIG. 1 is a view of a branch of 'Jork 57/201' showing leaves and fruit of the variety.
Figure 2:
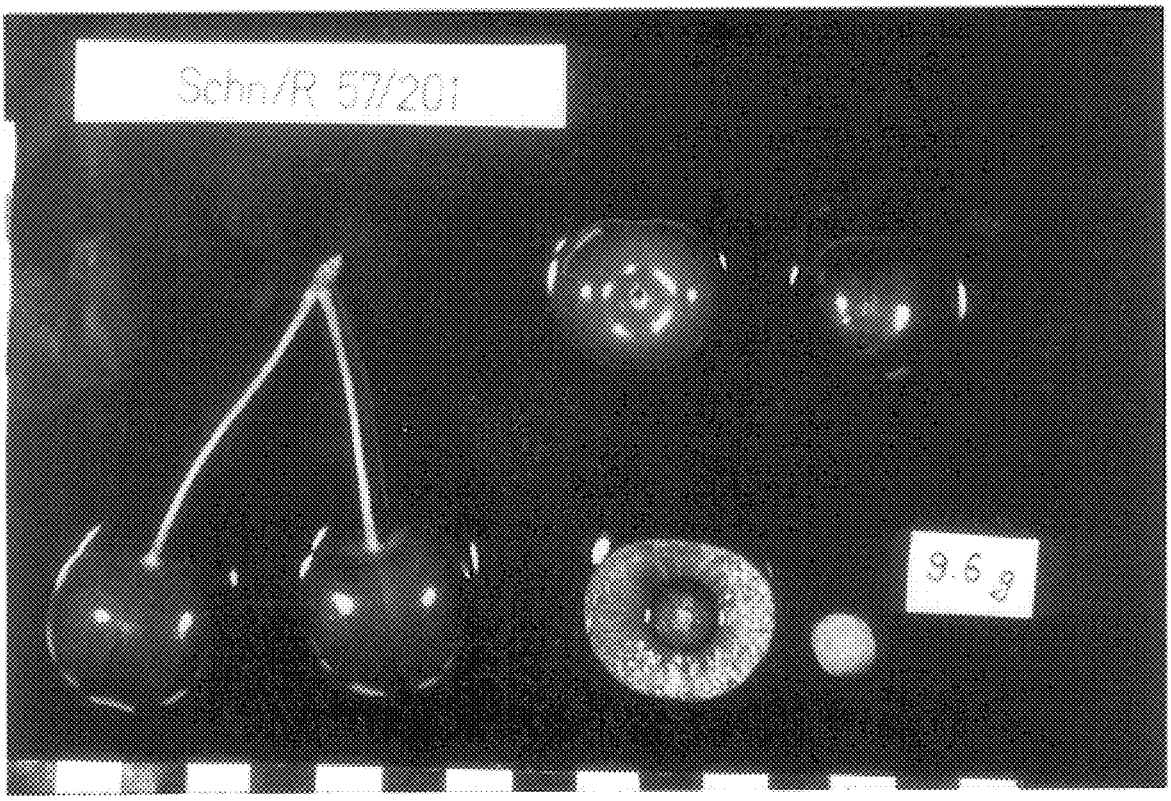
FIG. 2 shows (left) a side view of fruit and stems, (right, top) top (stem) and bottom end views of fruit, and (right, bottom) a cross-sectional view of a fruit and a pit of 'Jork 57/201'.

The following is a detailed description of my new variety of cherry tree based on trees produced under orchard practices in Jork, Germany, unless otherwise noted, and observed at this location.

Color references are made in accordance with The Royal Horticultural Society (R.H.S.) Colour Chart (1976) and in some cases to the Munsell Book of Color (MBC) where indicated, except where general color terms of ordinary dictionary significance are obvious.

All trees of the new variety, insofar as I have been able to observe them, have been identical in all the characteristics described below.

Genus and Species: *Prunus avium*, L. (sweet cherry).

Parentage: 'Schneiders Spate Knorpelkirsche' (seed parent)×'Rube' (pollen parent).

Propagation: Holds to distinguishing characteristics through succeeding propagation by grafting.

Dates of first and last picking: July 26th and August 6th, respectively, at the Fruit Experiment Station, Jork, Germany, about 14 days after 'Bing'.

Tree:

*Vigo.*—Boldly vigorous. In a rootstock trial in Jork, Germany, from 1989 through 1997, trees of my new variety at the end of the trail had trunks with an average diameter of 14.6 cm measured thirty centimeters above the ground.

*Habit.*—Upright, pyramidal in form due to strong apical dominance in the central leader.

*Shoots.*—Thick and long in young, nonbearing trees with numerous small lenticels arranged perpendicularly to the stem's main axis. In autumn, after cessation of terminal growth, the color of the bark at the fourth internode above the proximal position is grey-orange (R.H.S. 177A) on the side of the stem that is exposed to direct sunlight, grey-brown (R.H.S. 199A) on the other side (in contrast to stems of 'Bing', which are grey-orange (R.H.S. 165B) and grey-brown (R.H.S. 199B), respectively).

Leaves:

*Size.*—Mature leaves are very large, glabrous and smooth with adaxial lamella surface yellow green and abaxial surface yellow-green. When observed during one year the mature leaf averaged about 7.6 cm to 9.5 cm wide and about 14 cm long.

*Shape.*—Ellipsoid, tapering to a point.

*Color.*—In spring, before emergence and expansion, unfolded leaves are grey-red (R.H.S. 178B) on the abaxial surface and grey-brown (R.H.S. 199A) on both the abaxial and adaxial surfaces when they are about one-half unfolded. In contrast, the unfolded leaves of 'Bing' are grey-red (178C and, when the leaves are about one-half unfolded, yellow-green (R.H.S. 152B). Upper surface of mature leaf in one observation was green (MBC-Hue 5GY, value 4, Chroma 8). Lower surface of mature leaf in one observation was green (MBC-Hue 7.5 GY, Value 6, Chroma 8).

*Margin.*—Slightly rounded.

Glands: Present on both the petiole and proximal part of the leaf blade with a round shape. From 0–3 on most leaves.

Flowers: Flowers are borne on lateral spurs on branches that are two years old or older and/or near the proximal end of one-year-old twigs on axillary buds of long shoots. Also borne on axillary buds of shoots laid down the previous growing season. Typically, 3–5 flowers are produced from spur buds and 3–5 flowers are also borne on axillary buds on the previous season's shoots. In one season flowers were observed to have a typical diameter of about 3.2 cm. Open later than most other cultivars. In Jork, Germany, from 1996–1998, flowers on average: first opened on April 28$^{th}$; were in full bloom (80% of flowers open) by May 5$^{th}$; and ended (90% of flowers worn) May 14$^{th}$.

Color: White (MBC-Hue 2.5 PB, value 9, Chroma 2).

Number: Single.

Petals: 5.

Stamens: About 25.

Pedicels: About 3.8–4.0 cm long and of intermediate thickness, about 1 mm, compared with 'Bing', the pedicels of which are about 3.4 cm long. Yellow-green (R.H.S. 146A), compared with 'Bing' which are a lighter shade (R.H.S. 146B).

Anthers: Yellow.

Pollen: Yellow-orange.

Flowering period: About May 10 in Geneva, N.Y. (3–4 days later than 'Bing').

Pollination: Group II, i.e., pollen-compatible with sweet cherry varieties other that those within the pollination group designated Group II (S1S3).

Fruit:

*Color.*—Grey-purple (R.H.S. 187A) at full maturity, but red (R.H.S. 53A) at usual commercial harvest maturity.

*Size.*—About 25 mm high, about 23 mm wide, weighing from 8.0 to 10.5 g. Larger than most other late-season varieties.

*Shape.*—Slightly cordate.

*Flesh.*—Firmer than many other sweet cherry cultivars. Color usually one color shade lighter than the skin. Soluble solids level generally above 16 percent at maturity in East Wenatchee, Wash.

*Pit.*—Medium in size with protruding suture ridges. Fruit clingstone. Light to medium tan in coloration.

*Stem.*—Length averages 5.3 cm.

*Ripening.*—About August 1 in Geneva, N.Y.

*Sweetness and Acidity.*—The juice has a natural acidity level of pH 3.7 and titratable acidity of 0.43%.

*Flavor.*—Strongly cherry-like with a good balance of natural sugars and acidity coupled with high cherry essence.

*Fruiting habit.*—Trees that are grafted to the common cherry rootstock 'Mazzard' (believed to be unpatented) typically have flowers produced after 3–4 growing seasons on trees that have been planted in their orchard position. Crop loads on mature trees are usually less densely spaced than on 'Bing'. In Jork, Germany, July 1992–1997 trees grafted on 'F12/1' rootstock averaged about 17 kg of fruit per tree.

Other characteristics: Resists rain-induced splitting exceptionally well.

I claim:

1. A new and distinct variety of cherry tree, substantially as herein shown and described.

* * * * *